United States Patent [19]

Hayashi et al.

[11] 4,145,382

[45] Mar. 20, 1979

[54] PROCESS FOR PRODUCING POLYFLUOROALKYL PHOSPHATES

[75] Inventors: Takao Hayashi, Zushi; Shoichi Kawakami, Yokohama, both of Japan

[73] Assignee: Asahi Glass Company Ltd., Tokyo, Japan

[21] Appl. No.: 856,101

[22] Filed: Nov. 30, 1977

[30] Foreign Application Priority Data

Dec. 16, 1976 [JP] Japan .................................. 51/150359

[51] Int. Cl.$^2$ ................................................. C07F 9/09
[52] U.S. Cl. .................................... 260/987; 260/924; 260/925; 260/955
[58] Field of Search ................. 260/924, 925, 955, 987

[56] References Cited

U.S. PATENT DOCUMENTS

| | | | |
|---|---|---|---|
| 3,083,224 | 3/1963 | Brace et al. ...................... | 260/987 X |
| 3,422,166 | 1/1969 | Davis ................................ | 260/925 X |
| 3,425,912 | 2/1969 | Deutsch et al. .................. | 260/924 X |
| 4,029,722 | 6/1977 | Demarcq et al. ................. | 260/924 X |

*Primary Examiner*—Anton H. Sutto
*Attorney, Agent, or Firm*—Oblon, Fisher, Spivak, McClelland & Maier

[57] ABSTRACT

An aqueous dispersion of an ethanol amine salt of polyfluoroalkyl phosphate is prepared by using a polyfluoroalkanol, a phosphorus oxyhalide water and an ethanol amine. The process for producing a polyfluoroalkyl phosphate comprises the first step of reacting a polyfluoroalkanol containing small amount of water with phosphorus oxyhalide and the second step of producing a polyfluoroalkyl phosphate by hydrolyzing the reaction product and the third step of reacting the reaction product with ethanol amine in a large amount of water.

15 Claims, No Drawings

PROCESS FOR PRODUCING POLYFLUOROALKYL PHOSPHATES

BACKGROUND OF THE INVENTION

1. Field of the Invention

The present invention relates to a process for producing a polyfluoroalkyl phosphate. More particularly, it relates to a process for producing a polyfluoroalkyl phosphate as an aqueous dispersion of an ethanol amine salt of polyfluoroalkyl phosphate by using a polyfluoroalkanol, a phosphorus oxyhalide, water and an ethanol amine.

2. Description of the Prior Arts

The ethanol amine salts of polyfluoroalkyl phosphates obtained by the process of the present invention are the polyfluoroalkyl phosphates having the formula

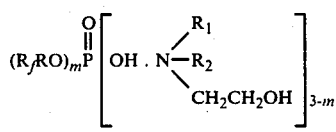

wherein $R_f$ represents a $C_5$-$C_{14}$ perfluoroalkyl group; R represents a $C_1$-$C_4$ divalent alkylene group; $R_1$ and $R_2$ respectively represent hydrogen atom or —$CH_2CH_2OH$; and m represents an average of 1 to 2.5.

It has been known that the polyfluoroalkyl phosphates have useful characteristics as water soluble surfactants and oil-repellent agents for fabrics, paper and a like as disclosed in Japanese Patent Publication No. 4770/1973 and U.S. Pat. No. 3,083,224.

In Japanese Patent Publication No. 4770/1973, the following processes for producing polyfluoroalkyl phosphates have been disclosed.

The process for reacting a polyfluoroalkanol with a phosphorus oxyhalide. The process for reacting a polyfluoroalkanol with phosphorus pentachloride. The process for reacting a polyfluoroalkanol with a dialkyl phosphite. There is also the disclosure that the reaction of a polyfluoroalkanol with a phosphorus oxyhalide is carried out in the presence of a tertiary amine and aprotonic solvent at 0 to 110° C.

In accordance with the studies of the inventors, the process for producing the polyfluoroalkyl phosphate by reacting the polyfluoroalkanol with the phosphorus oxyhalide has the following disadvantages.

It has been found that suitable oil-repellency could not be imparted in the treatment of paper etc. by using the polyfluoroalkyl phosphate obtained by reacting the polyfluoroalkanol with the phosphorus oxyhalide and hydrolyzing the resulting polyfluoroalkyl phosphohalide to produce a polyfluoroalkyl phosphate and reacting it with an ethanol amine.

These disadvantages could not be overcome by reacting the polyfluoroalkanol with the phosphorus oxyhalide in the presence of the tertiary amine and aprotonic solvent such as benzene, tetrahydrofuran and dioxane.

SUMMARY OF THE INVENTION

The inventors have studied various processes for reacting a polyfluoroalkanol with a phosphorus oxyhalide under the consideration of the above-mentioned problems and have found the following interest facts.

The oil-repellency can be remarkably improved by using ethanol amine salts of polyfluoroalkyl phosphates which are produced by reacting a polyfluoroalkanol containing small amount of water with a phosphorus oxyhalide and producing polyfluoroalkyl phosphohalide in a form of partially hydrolyzed product and then, hydrolyzing it and reacting with an ethanol amine.

The inventors have also found that it is important to obtain an aqueous dispersion of an ethanol amine salt of polyfluoroalkyl phosphate by reacting the polyfluoroalkyl phosphate with an ethanol amine in the presence of a large amount of water.

The present invention has been attained by these novel findings.

The objects of the present invention have been attained by providing a process for producing a polyfluoroalkyl phosphate as an aqueous dispersion of an ethanol amine salt of polyfluoroalkyl phosphate having the formula

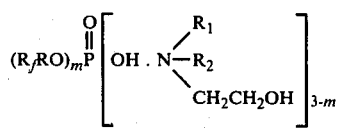

wherein $R_f$ represents a $C_5$-$C_{14}$ perfluoroalkyl group; R represents a $C_1$-$C_4$ divalent alkylene group; $R_1$ and $R_2$ respectively represent hydrogen atom or —$CH_2CH_2OH$ and m represents an average of 1 to 2.5; by reacting a polyfluoroalkanol having the formula $R_fROH$ with a phosphorus oxyhalide in the presence of water; and hydrolyzing the partially hydrolyzed polyfluoroalkyl phosphohalide to produce the polyfluoroalkyl phosphate and then, reacting the resulting polyfluoroalkyl phosphate with an ethanol amine in the presence of a large amount of water.

It is also possible to simultaneously perform the reaction for producing the polyfluoroalkyl phosphohalide and the hydrolysis of the reaction product by using a polyfluoroalkanol containing suitable amount of water for the hydrolysis.

DETAILED DESCRIPTION OF THE PREFERRED EMBODIMENTS

In the process of the present invention, it is important to carry out the reaction of a polyfluoroalkanol with a phosphorus oxyhalide in the presence of water. When the reaction is carried out without an addition of water, the oil-repellency of the resulting ethanol amine salt of polyfluoroalkyl phosphate is inferior. The reason is not clear and it may be because of thermal instability of the polyfluoroalkyl phosphohalide. For example, in said reaction, a by-product of oligomer such as

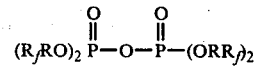

is easily produced by a thermal decomposition of the product.

The partial hydrolysis of the product is performed in the presence of water whereby the polyfluoroalkyl phosphohalide is stabilized. The present invention is not limited by the description.

In the present invention, the partially hydrolyzed polyfluoroalkyl phosphohalide is hydrolyzed to produce polyfluoroalkyl phosphate and the product is converted into the ethanol amine salt by reacting it with ethanol amine.

It is also important to carry out the reaction of the polyfluoroalkyl phosphate with ethanol amine in the presence of a large amount of water. In the process of the present invention, it is preferable to carry out the reaction of the polyfluoroalkyl phosphate with ethanol amine, with 400 to 500 wt.% of water to the polyfluoroalkyl phosphate. When the amount of water is not enough, a viscosity of the reaction system is remarkably high so as to prevent a homogeneous reaction and to prevent a smooth reaction. It is possible to carry out a homogeneous and smooth reaction under low viscosity conditions by adding an organic solvent such as dioxane. However, the oil-repellency is not satisfactory when the resulting solution of the ethanol amine salt of polyfluoroalkyl phosphate is used.

In the process of the present invention, the polyfluoroalkanols having the formula $R_fROH$ can be selected from the known compounds. In the formula, $R_f$ is a $C_5$–$C_{14}$ especially $C_6$–$C_{12}$ perfluoroalkyl group and R is a $C_1$–$C_4$ especially $C_1$–$C_2$ divalent alkylene group and $R_f$ and R can be respectively straight chain type or branched chain type group. The mixture of polyfluoroalkanols having different carbon atoms of $R_f$ can be used in the process of the present invention.

The phosphorous oxyhalide is preferably phosphorous oxychloride because of easy availability. Thus, it is possible to use phosphorus oxybromide and phosphorus oxychlorobromide.

In the process of the present invention, the reaction of the polyfluoroalkanol with the phosphorus oxyhalide is carried out at a molar ratio of the polyfluoroalkanol: the phosphorus oxyhalide of 1.0 to 2.5:1.0 preferably 1.5 to 1.8:1.0.

In the reaction, water should be added. It is preferable to add water at a molar ratio of water: the phosphorus oxyhalide of 0.2 to 2.0:1.0, preferably 0.5 to 1.0:1.0. The reaction temperature is in a range of 70 to 100° C. preferably 80 to 90° C. The reaction time is in a range of 1 to 4 hours preferably about 2 to 3 hours. When the reaction temperature is lower, the viscosity is too high or the foaming is caused whereby the stirring is difficult. When the reaction temperature is higher or the reaction time is longer, the side reaction is highly caused to increase the production of oligomer etc. whereby the oil-repellency of the product is inferior.

In the first step reaction, the partially hydrolyzed polyfluoroalkyl phosphohalide has the formula

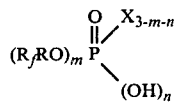

wherein $R_f$, R and m are defined above and n represents an average of 0.2 to 2.0 and X represents a halogen atom.

Then, the partially hydrolyzed polyfluoroalkyl phosphohalide is completely hydrolyzed to produce the polyfluoroalkyl phosphate having the formula

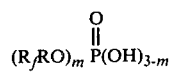

The second step reaction is carried out at a molar ratio of water: the partially hydrolyzed polyfluoroalkyl phosphohalide of 1.3 to 5.0:1.0 preferably 2.0 to 3.0:1.0.

The reaction temperature is in a range of 70 to 100° C. preferably 80 to 90° C. The reaction time is in a range of 0.5 to 4 hours preferably 1 to 2 hours.

In the first and second step reactions, hydrogen halide such as HCl is produced as a by-product. In the process of the present invention, it is preferable to substantially separate the by-product of hydrogen halide. When the hydrogen halide remains, it reacts with ethanol amine to produce the salt in the third step reaction whereby the smooth and advantageous reaction of the polyfluoroalkyl phosphate with ethanol amine is adversely affected and the oil-repellency and the viscosity of the product are deteriorate. The by-product of hydrogen halide can be purged with an inert gas such as nitrogen gas. For example, the by-product of hydrogen halide can be substantially removed from the reaction system by carrying out the first and second step reactions under introducing an inert gas.

In the process of the present invention, it is possible to carry out the separation of the by-product of hydrogen halide under using an acid acceptor such as a tertiary amine which has no functional group as disclosed in Japanese Patent Publication No. 4770/1973. However, it is preferable to employ the method of purging with the inert gas since the acid acceptor such as the tertiary amine should be separated from the reaction system and the residue of the acid acceptor or the hydrogen halide-acid acceptor salt causes the similar disadvantages in the third step reaction.

In the process of the present invention, the reaction of the polyfluoroalkyl phosphate with ethanol amine is carried out in the presence of a large amount of water as the third step reaction. The third step reaction is carried out at a molar ratio of ethanol amine : polyfluoroalkyl phosphate of 1.5 to 5.0:1.0 preferably 2.0 to 3.0:1.0 and a ratio of water to the polyfluoroalkyl phosphate of more than 200 wt.% preferably about 400 to 600 wt.%. When the amount of water is too small, the viscosity of the reaction system is too high and a smooth, the homogeneous reaction cannot be conducted whereby the object product can not be obtained in a form of an aqueous dispersion which is advantageous. When the amount of water is too small, the oil-repellency of the product is not satisfactory.

In the third step reaction, the reaction temperature is in a range of the room temperature to 100° C.

In the process of the present invention, it is important to keep the temperature of higher than 80 to 100° C. in order to give stable dispersion of the ethanol amine salt resulted in the third step reaction in water. The time for keeping the temperature of higher than 80° C. is in a range of 3 to 12 hours preferably 5 to 8 hours. Accordingly, it is usual to keep the temperature of higher than 80° C. during at least later half time in the third step reaction. It is possible to keep the temperature of higher than 80° C. during the full time in the third step reaction. It is also possible to keep low temperature during the former half time in the third step reaction. For example, it is possible to react them at the room temperature to 100° C. preferably 30 to 60° C. for 1 to 3 hours preferably 1 to 2 hours and then, to react them at 80 to 100° C. for 3 to 12 hours preferably 5 to 8 hours.

The ethanol amines used in the third step reaction can be monoethanol amine, diethanol amine and triethanol amine which can be a mixture thereof.

In the process of the present invention, the addition of aprotonic solvent to the reaction system is disadvantageous for the oil-repellency of the product. Accordingly, it is not preferable to use such organic solvent.

In the third step reaction, when the resulting ethanol amine salt is not kept at higher than 80° C. or the time for keeping it at higher than 80° C. is too short, the dispersion of the ethanol amine salt is not stable and the oil-repellency of the product is not satisfactory. Thus, the ethanol amine salt of polyfluoroalkyl phosphate having the formula

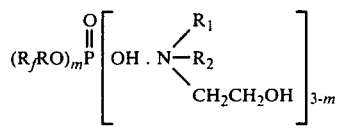

can be obtained in a form of an aqueous dispersion. In the formula, $R_f$ and R are defined above and $R_1$ and $R_2$ are respectively hydrogen atom or $-CH_2CH_2OH$ and m is an average of 1 to 2.5.

The aqueous dispersion of the ethanol amine salt is preferably prepared to have a viscosity of about 50 to 250 cp.

The polyfluoroalkyl phosphates obtained by the process of the present invention are especially effective as an oil-repellent agent. For example, they can be used for the oil-repellent treatments for various solid products such as fabrics, yarns, leathers, paper, plastic sheets, woods, ceramics, clays and articles made of these materials such as cloths, wall paper, paper bags, paper boxes, and porous porcelains. They are especially effective for the oil-repellent treatment for oily food packaging paper or containers for packaging margarines, doughnuts, chocolates and dog foods.

In their application for oil-repellency purposes, the bis(fluoroalkyl) phosphates (i.e. m=2) of this invention are immensely more effective than the mono compounds (i.e. m=1), and where mixtures are unavoidable, it is preferred to use such mixtures wherein the bis(fluoroalkyl) compounds predominate (i.e. m has an average value greater than 1.5). Fully alkylated phosphates (i.e. m=3) do not impart oil repellency, but where a mixture is more economically available, they constitute an inert, but harmless diluent to the active bis-compounds. Therefore, mixtures of polyfluoroalkyl phosphates having a m-value greater than 2, say up to m=2.5 are tolerable. Altogether, an average m-value between 1 to 2.5 can be used.

In the process of the present invention, it is preferable to produce the ethanol amine salt of polyfluoroalkyl phosphate in a form of an aqueous dispersion at a concentration of 5 to 30 wt.% preferably about 15 to 20 wt.% as the third step reaction product. It is also possible to dilute it when it is used for the oil-repellent treatment. In usual, it is preferable to use it at a concentration of about 0.3 to 1.0 wt.% of the polyfluoroalkyl phosphate as an aqueous dispersion, when it is used for the purpose of oil-repellent treatment for paper. It can be added in the sheeting process and it can be also applied by the pading process, the spraying process, the bush-coating process and the immersion process.

Without limiting the present invention, the following examples are given to illustrate the preferred method of preparation. Parts and percents mentioned are by weight.

EXAMPLE 1

In a 300 ml flask equipped with a stirrer, a dropping funnel, a thermometer and a nitrogen inlet tube, 44.5 g of phosphorous oxychloride was charged and it was heated to 85° C. under feeding dry nitrogen gas and 200 g of $C_6F_{17}CH_2CH_2OH$ containing 0.6% of water was added dropwise through the dropping funnel during 60 minutes. The mixture was further stirred at 85° C. for 1 hour and then 5 g of water was added dropwise during 15 minutes. The reaction was continued until no hydrogen chloride was evolved. A 80 g of the resulting intermediate was added dropwise to an aqueous solution containing 22 g of diethanol amine and 395 g of water at 85° C. during 15 minutes. The temperature rised to 90° C. by the exothermic reaction. The mixture was stirred for 10 hours and when the viscosity decreased to 30 cp., the reaction was stopped. The reaction product was confirmed to be the compound having the formula

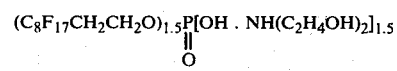

by the infrared spectrum analysis.

EXAMPLE 2

In accordance with the process of Example 1 50 g of the intermediate was neutralized with an aqueous solution of monoethanol amine to obtain 280 g of 20% an aqueous dispersion of the compound having the formula

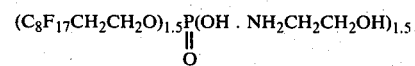

EXAMPLE 3

In accordance with the process of Example 1,50 g of the intermediate of Example 1 was neutralized with an aqueous solution of triethanol amine to obtain 320 g of 20% an aqueous dispersion of the compound having the formula

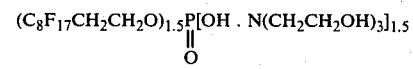

EXAMPLE 4

A compound having the formula

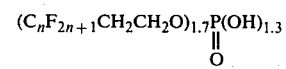

was obtained by reacting 100 g of a compound having the formula

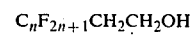

wherein n is respectively 6, 8, 10 and 12 at ratios of 20%, 45%, 22% and 13% and 17 g of phosphorus oxychloride and 3.5 g of water and then, the product was neutralized with an aqueous solution of diethanol amine at 90° C. for 10 hours to obtain an aqueous dispersion of a compound having the formula

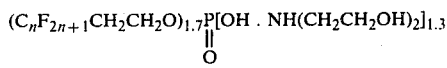

Reference 1

In a 300 ml flask equipped with a stirrer, a dropping funnel, a thermometer and a nitrogen inlet tube, 11 g of phosphorus oxychloride and 50 g of tetrahydrofuran were charged and 50 g of $C_8H_{17}CH_2CH_2OH$ containing 0.6% of water was added dropwise through the dropping funnel during 60 minutes under feeding dry nitrogen gas to react them at 50° C. and the reaction was continued for further 1 hour. When the generation of hydrogen chloride was stopped, 1.5 g of water was added dropwise during 15 minutes and the mixture was stirred for 30 minutes and a solution containing 15 g of diethanol amine, 20 g of tetrahydrofuran and 80 g of water was added dropwise to produce the diethanol amine salt. After 30 minutes, it was cooled to the room temperature to obtain 338 g of pale yellow transparent solution.

Reference 2

In a 100 ml flask equipped with a stirrer, a dropping funnel, a thermometer and a nitrogen inlet tube, 11 g of phosphorus oxychloride was charged and it was heated to 85° C. under feeding dry nitrogen gas and 50 g of $C_8F_{17}CH_2CH_2OH$ containing 0.02% of water was added dropwise through the dropping funnel during 60 minutes and the reaction was continued for further 1 hour and then, 2 g of water was added during 15 minutes to the reaction mixture at 85° C. and the reaction was continued until no hydrogen chloride was evolved. The resulting intermediate was added dropwise to an aqueous solution containing 15 g of diethanol amine and 250 g of water during 15 minutes and the temperature was raised to 90° C. and the mixture was stirred for 10 hours. The viscosity of the dispersion at room temperature was 85 cp.

Tests

Oil-repellencies of the aqueous dispersion of the polyfluoroalkyl phosphate prepared by the process of the present invention and the aqueous solution or dispersion of the polyfluoroalkyl phosphate prepared in the processes of References 1 and 2 were compared by the following method.

A 1 g of 1% aqueous solution of polyethyleneimine was gradually added to 200 g of 1% aqueous dispersion of kraft pulp and the mixture was stirred and 10 g of 0.1% aqueous dispersion of the polyfluoroalkyl phosphate was added dropwise to the mixture and the mixture was further stirred for 5 minutes and sheeted by a standard hand-made paper machine of Japanese Industrial Standard P 8209. The wet paper was pressed between two sheets of filter paper to absorb water and the paper was dried by a drum type drier at 100° C. for 60 minutes to prepare oil-repellent paper-sheets.

The oil-repellency was measured as follows.

One drop of the test oil shown in Table 1 was put on the treated paper and the condition of permeation of oil after 15 seconds was observed. The oil-repellency of the treated paper was rated by the maximum rating in no permeation. Higher number shows higher oil-repellency.

The oil-repellencies of the treated papers treated with each of the polyfluoroalkyl phosphates obtained in Examples 1 to 4 and References 1 and 2 are shown in Table 2.

Table 1

| Oil-repel-lency | Test oils for oil-repellency | | |
| --- | --- | --- | --- |
|  | Castor oil vol. % | Toluene vol. % | Heptane vol. % |
| 1 | 100 | 0 | 0 |
| 2 | 90 | 5 | 5 |
| 3 | 80 | 10 | 10 |
| 4 | 70 | 15 | 15 |
| 5 | 60 | 20 | 20 |
| 6 | 50 | 25 | 25 |
| 7 | 40 | 30 | 30 |
| 8 | 30 | 35 | 35 |
| 9 | 20 | 40 | 40 |
| 10 | 10 | 45 | 45 |
| 11 | 0 | 50 | 50 |
| 12 | 0 | 45 | 55 |

Table 2

| Polyfluoroalkyl phosphate | Oil-repellency |
| --- | --- |
| Example 1 | 12 |
| Example 2 | 12 |
| Example 3 | 11 |
| Example 4 | 12 |
| Reference 1 | 7 |
| Reference 2 | 9 |

EXAMPLE 5

In a 500 ml four necked flask equipped with a stirrer, a dropping funnel, a thermometer and a nitrogen inlet tube, 100 g of $C_8F_{17}CH_2CH_2OH$ and 2.6 g of water were charged and heated to 85° C. under feeding oxychloride nitrogen gas and 22 g of phosphorus oxychoride was added dropwise through a dropping funnel during 60 minutes and the reaction was continued for 60 minutes. The resulting intermediate was added dropwise to an aqueous solution containing 30 g of diethanol amine and 450 g of water at 50° C. to neutralize it. At 50° C., the mixture was stirred for 1 hour to uniformly disperse the product and then, the temperature was raised to 90° C. and the mixture was further stirred for 6 hours.

In accordance with the method mentioned before, the pulp was treated with the product and the oil-repellency of the paper was tested to give the oil-repellency of 12.

What is claimed is:

1. A process for producing a polyfluoroalkyl phosphate as an aqueous dispersion of an ethanolamine salt thereof having the formula

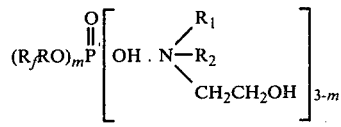

wherein $R_f$ represents a $C_5$–$C_{14}$ perfluoroalkyl group; $R_1$ and $R_2$ each represent hydrogen or —$CH_2CH_2OH$; R represents a $C_1$–$C_4$ divalent alkylene group; and m represents a value within the range of 1 to 2.5, which comprises:

(a) reacting a polyfluoroalkanol having the formula $R_fROH$ with a phosphorous oxyhalide in the presence of water in amounts consistent with the ratio of corresponding components in said salt above under reaction conditions which minimize the production of oligomer by-product, which maintain the viscosity of the reaction solution at desirable levels and which avoid foaming of the reaction solution;

(b) hydrolyzing the partially hydrolyzed polyfluoroalkylphosphophalide obtained under conditions which effect the formation of the desired perfluoroalkylphosphate, said steps (a) and (b) being conducted under conditions which remove hydrogen halide eliminated in the reactions from the reaction solutions; and (c) reacting the polyfluoroalkylphosphate product obtained with an ethanolamine in a quantity of water sufficient to maintain an acceptable viscosity of reaction solution to ensure a smooth and homogeneous reaction and sufficient to yield a product solution which when applied to a substrate exhibits the desired degree of water repellency.

2. The process of claim 1, wherein the molar ratio of the polyfluoroalkanol: phosphorus oxyhalide : water reactants in step (a) range from 1.0 to 2.5:1:0.2 to 2.0.

3. The process of claim 1, wherein the hydrolysis reaction of step (b) is conducted at a molar ratio of water to the partially hydrolyzed polyfluoroalkyl phosphohalide of 1.3 to 5.0:1.0.

4. The process of claim 1, wherein the molar ratio of the ethanol amine to polyfluroalkyl phosphate reactants in step (c) range from 1.5 to 5.0:1.0 in the presence of more than 200 wt.% of water based on the quantity of polyfluoroalkyl phosphate reactant present.

5. The process of claim 1, wherein the reaction of step (c) is conducted under conditions in which at least some time during the reaction the resulting ethanol amine salt of the polyfluoroalkyl phosphate is subjected to a temperature greater than 80° C.

6. The process of claim 1, wherein the reaction of the polyfluoroalkanol, the phosphorus oxyhalide and water in step (a) is conducted at a temperature of 70° to 100° C.

7. The process of claim 1, wherein the hydrolysis reaction of step (b) is conducted at a temperature of 70° to 100° C.

8. The process of claim 1, wherein the reaction of step (c) is conducted at a temperature of 80° to 100° C.

9. The process of claim 1, wherein the by-product hydrogen halide is substantially removed from the polyfluoroalkylphosphate product of step (b) prior to the reaction of step (c).

10. A process for producing a polyfluorophosphate as an aqueous dispersion of an ethanolamine salt thereof having the formula

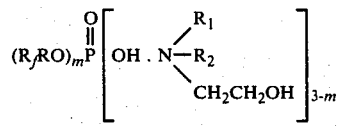

wherein $R_f$ represents a $C_5$–$C_{14}$ perfluoroalkyl group; R represents a $C_1$–$C_4$ divalent alkylene group; $R_1$ and $R_2$ each represent hydrogen or —$CH_2CH_2OH$; and m represents a value within the range of 1 to 2.5, which comprises:

(a) reacting a polyfluoroalkanol having the formula $R_fROH$ with a phosphorous oxyhalide in the presence of water in a molar ratio of 1.0 to 2.5:1.0:0.2 to 2.0 under reaction conditions which minimize the production of oligomer by-product, which maintain the viscosity of the reaction solution at desirable levels and which avoid foaming of the reaction solution;

(b) hydrolyzing the partially hydrolyzed polyfluoroalkylphosphohalide obtained under conditions which effect the formation of the desired perfluoroalkylphosphate, said steps (a) and (b) being conducted under conditions which remove hydrogen halide eliminated in the reactions from the reaction solutions; and (c) reacting the polyfluoroalkylphosphate product obtained with an ethanolamine in a quantity of water sufficient to maintain an acceptable viscosity of reaction solution to ensure a smooth and homogeneous reaction and sufficient to yield a product solution which when applied to a substrate exhibits the desired degree of water repellency.

11. The process of claim 10, wherein the molar ratio of the polyfluoroalkanol: phosphorous oxyhalide: water reactants in step (a) ranges from 1.5 to 1.8:1.0:0.5 to 1.0.

12. A process for producing a polyfluoroalkylphosphate as an aqueous dispersion of an ethanolamine salt thereof having the formula

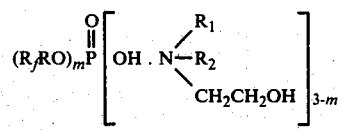

wherein $R_f$ represents a $C_5$–$C_{14}$ perfluoroalkyl group; R represents a $C_1$–$C_4$ divalent alkylene group; $R_1$ and $R_2$ each represent hydrogen or —$CH_2CH_2OH$; and m represents a value within the range of 1 to 2.5, which comprises:

(a) reacting a polyfluoroalkanol having the formula $R_fROH$ with a phosphorous oxyhalide in the presence of water in a molar ratio of 1.0 to 2.5:1.0:0.2 to 2.0 at a reaction temperature of 70° to 100° C. for 1 to 4 hours;

(b) hydrolyzing the partially hydrolyzed polyfluoroalkylphosphohalide obtained with water in a mole ratio of 1.0:1.3 to 5.0 at a reaction temperature of 70° to 100° C. for 0.5 to 4 hours; and (c) reacting the polyfluoroalkylphosphate product obtained with an ethanolamine in a quantity of water sufficient to maintain an acceptable viscosity of reaction solution to ensure a smooth and homogeneous reaction and sufficient to yield a product solution which when applied to a substrate exhibits the desired degree of water repellency.

13. The process of claim 12, wherein the molar ratio of the polyfluoroalkanol: phosphorous oxyhalide: water reactants in step (a) range from 1.5 to 1.8:1.0:0.5 to 1.0.

14. The process of claim 12, wherein the molar ratio of water to partially hydrolyzed polyfluoroalkylphosphohalide in step (b) range from 2.0 to 3.0:1.0.

15. The process of claim 12, wherein the reaction temperature of steps (a) and (b) ranges from 80° to 90° C.

* * * * *